US005362904A

United States Patent [19]
Kearns

[11] Patent Number: 5,362,904
[45] Date of Patent: Nov. 8, 1994

[54] PROCESS FOR THE PREPARATION OF ACRYLIC ACID AND METHACRYLIC ACID ESTERS

[75] Inventor: Mark A. Kearns, Sutton, England

[73] Assignee: International Speciality Chemicals Limited, Hythe, Great Britain

[21] Appl. No.: 950,344

[22] Filed: Sep. 24, 1992

[30] Foreign Application Priority Data

Sep. 27, 1991 [GB] United Kingdom ............... 9120584

[51] Int. Cl.$^5$ ............................................. C07C 67/02
[52] U.S. Cl. ................................................... 560/217
[58] Field of Search ........................................ 560/217

[56] References Cited
FOREIGN PATENT DOCUMENTS
2163149 2/1986 United Kingdom .

*Primary Examiner*—Paul J. Killos
*Attorney, Agent, or Firm*—Fay, Sharpe, Beall, Fagan, Minnich & McKee

[57] ABSTRACT

This invention relates to a process for the preparation of esters of acrylic or methacrylic acid with alcohols. The process comprises reacting the preformed ester of a $C_1$-$C_4$ monohydric alcohol having only one oxygen function under transesterification conditions with a second alcohol having at least two carbon atoms and at least two oxygen functions in the presence of a catalyst comprising (a) an oxide, hydroxide or nitrate of calcium or barium and (b) a lithium compound LiX wherein X is nitrate, sulphite or carboxylate having more than six carbon atoms such that both (a) and (b) are not nitrate in the same catalyst.

2 Claims, No Drawings

PROCESS FOR THE PREPARATION OF ACRYLIC ACID AND METHACRYLIC ACID ESTERS

The present invention relates to a process for the preparation of esters of acrylic acid or methacrylic acid with alcohols.

Acrylic and methacrylic acid esters of alcohols have a wide and varied use in the market place, ranging from use in the paint industry to the application of such esters in the adhesive industry. It is therefore of great advantage to operate a process wherein the yield of ester is in excess of 98%.

Typically, the production of the acid esters of alcohols is carried out via the transesterification reaction where the methacrylic or acrylic acid ester is reacted with an alcohol in the presence of a catalyst. A problem often encountered with this process is the presence of partially esterified esters in the final product. Typically, when a trihydric alcohol such as trimethylol propane is used as the alcohol reactant, there is often a low concentration of triesters. These partially esterified esters are difficult to isolate and often lead to undesired side reactions during use.

In trying to overcome the aforementioned problems, U.S. Pat. No. 4672105 discloses a transesterification process for producing high yields of triesters of acrylic acid or methacrylic acid with polyhydric alcohols by contacting the reaction mixture with a co-catalyst which comprises lithium halide and calcium oxide.

While the cited process provides high yields of the desired product, it has been found that the use of a lithium halide, and in particular lithium chloride, can result in corrosion and subsequent stress cracking of e.g. the 316 stainless steel reaction chamber. Alternatively, to overcome this problem, the reaction chamber may be lined with a glass layer. This however is less robust and introduces the possibility of cracks or fractures.

We have discovered that the transesterification process may be carried out to provide high yields of esters and overcome the aforementioned operating difficulties by using a co-catalyst which comprises a lithium salt and an oxide or hydroxide of calcium or barium.

Accordingly, the present invention provides a process for the preparation of acrylic acid or methacrylic acid esters of an alcohol which has at least 2 carbon atoms and at least two oxygen functions which process comprises reacting under tranesterification conditions a first reactant which is a preformed ester of (meth)acrylic acid and a $C_1$ to $C_4$ monohydric alcohol having only one oxygen function with a second reactant which is an alcohol having at least 2 carbon atoms and at least two oxygen functions in the presence of a catalyst composition comprising:

a) an oxide, hydroxide or a nitrate of calcium or barium b) a lithium compound LiX wherein X in LiX is selected from the anions nitrate, sulphite and a carboxylate having more than 6 carbon atoms such that both (a) and (b) are not nitrates in the same catalyst.

The first reactant, a preformed ester, used in the transesterification process is suitably an ester of a $C_1$ or $C_2$ monohydric alcohol such as methanol or ethanol.

The second reactant in the transesterification reaction is an alcohol which has at least 2 carbon atoms and at least two oxygen functions. By the expression "at least two oxygen functions" is meant here and throughout the specification that the second reactant has in addition to the oxygen function in the —OH group at least one other oxygen function which may be in the form of additional —OH groups, ether groups or carboxyl groups or any combinations of these. Specific examples of such second reactants include di- and polyhydric alcohols which have 2 or more carbon atoms, e.g. ethylene glycol, isopropylideneglycerol, 1,3-butylene glycol, trimethylolpropane, glycerol, pentaerythritol, dipentaerythritol, ditrimethylolpropane and tetrahydrofurfuryl alcohol. Additionally or alternatively, the alkoxylated derivatives of some of the di- and or polyhydric alcohols can also be used as the second reactant in the transesterification reactions of the present invention.

The preformed ester (first reactant) and the alcohol (second reactant) may be suitably mixed together prior to contact with the catalyst composition. The first reactant is suitably present in excess, e.g. in an excess of 2–5 times the stoichiometric amount of the second reactant, preferably 2–3 times.

The reactants are suitably dried prior to contact with the catalyst composition for the purposes of transesterification.

The reactants are suitably dried using techniques well known to those skilled in the art e.g. by the use of azeotropic distillation, molecular sieves, zeolites, silica gel etc.

The use of a stabiliser or polymerisation inhibitor is not essential in the present process. However, if desired, small amounts of an inhibitor such as e.g. para-methoxy phenol can be added to the reactants in amounts from 10–1000ppm, preferably in the range from 100–600ppm.

The catalyst composition comprises two components namely:

a) an oxide, hydroxide or nitrate of calcium or barium and b) a lithium compound LiX.

Where the anion X of LiX is a carboxylate, it is suitably selected from aliphatic or aromatic carboxylates, and is preferably a monocarboxylate selected from an octanoate, 2-ethyl hexanoate, a stearate and a benzoate.

The preferred catalyst composition comprises a mixture of lithium nitrate and calcium oxide.

The catalyst composition is suitably prepared by intimately mixing the two components. In the composition, the weight ratio of component (b) to component (a) is suitably in the range from 0.1:10 to 10:0.1 w/w and preferably from 1:3 to 1:4 w/w.

The catalyst composition is suitably used in an amount from 0.1 to 30% w/w, preferably from 0.5 to 10% w/w based on the second reactant.

The catalyst composition may be added to the reaction mixture as a single dose initially at the start of the reaction or in two or more aliquots over the duration of the reaction.

When the catalyst composition is a mixture of lithium nitrate and calcium oxide, it has been found that there is no need to add any additional polymerisation inhibitor such as a para-methoxy phenol.

This is an unexpected feature of the present invention.

The transesterification reaction may be carried out in the presence or in the absence of a suitable solvent. Usually no solvent is required.

The reaction is suitably carried out at atmoshperic pressure and at a temperature from 80°–120° C., preferably from 95°–115° C. If the reaction is carried out under a vacuum, the temperature used would be in the region of 60°–100° C.

A by-product of the transesterification reaction is the monohydric alcohol generated from the first reactant. In the case of the first reactant being a methyl acrylate or methyl methacrylate, the by-product alcohol would be methanol. Such by-products can be removed from the reaction as an azeotrope with the first reactant by e.g. azeotropic distillation. It is preferable to remove such by-product alcohols continuously from the reaction mixture as soon as it is formed.

The products of the present process are esters of (meth)acrylic acid with $C_2$ or higher alcohols used as the second reactant. Typically, the products that can be produced by this process include, trimethylol propane trimethacrylate (TMPTMA), diethylene glycol dimethyacrylate (DEGDMA), tetrahydrofurfuryl methacrylate (THFMA), 1,3-butylene glycol dimethacrylate (1,3-BGDMA) and ethylene glycol dimethacrylate (EGDMA).

The products of the present invention can yield these esters in an excess of 98% w/w. In the case of TMPTMA the crude product had an assay of 90–96 weight percent.

The crude esters so produced can be purified by filtration and washing to remove any traces of catalyst impurities present therein.

The process of the present invention is further illustrated with reference to the following Examples:

moving a water/methyl methacrylate mixture overhead at a temperature from 83°–99° C.

The first catalyst dose comprising lithium nitrate (1.2 g) and calcium oxide (3.6 g) was added to the hot reaction mixture and the resultant reaction mixture was heated to 95°–110° C. Under these conditions an azeotropic mixture of methanol and methyl methacrylate was removed overhead from the column at a head temperature of 67°–99° C. The methyl methacrylate thus recovered was recycled back to the reaction mixture after removal of methanol therefrom to maintain a good boil-up and a reaction temperature between 100° and 120° C.

Further doses of lithium nitrate (0.6 g) and calcium oxide (1.8 g) were added after 2.5 hours, and lithium nitrate (1.2 g) and calcium oxide (3.6 g) after 4 hours on stream when rate of generation of methanol in the reaction decreased significantly.

After about 10 hours, the reaction was completed and excess methyl methacrylate was distilled off under vacuum. The reaction mixture was then cooled and filtered using a filtering aid. The crude ester product so formed was treated with 0.5% w/w of carbon to absorb any dissolved catalytic compounds and finally filtered again.

The resultant product, upon assay using a capillary GC, showed that 95% of trimethylolpropane trimethacrylate had been formed. The reaction conditions and yields are tabulated below:

| Cat w/w | Cat % on TMP | $Li^+:Ca^{++}$ Mol ratio | Reflux Time Min | GC Anal. (%) | | | |
|---|---|---|---|---|---|---|---|
| | | | | TMPMMA | TMPDMA | TMPTMA | Adduct |
| LiNO3:CaO (1:3) | 3.75 | 1:3.7 | 690 | 0.15 | 3.2 | 91.2 | 4.6 |

| | |
|---|---|
| Methyl methacrylate | MMA |
| Trimethylolpropane | TMP |
| Trimethylolpropane monomethacrylate | TMPMMA |
| Trimethylolpropane dimethacrylate | TMPDMA |
| Trimethylolpropane trimethacrylate | TMPTMA |
| Ethylene glycol | EG |
| Li-Octoate | Lithium Octanoate |
| 1,3-Butylene glycol | BG |
| 1,3-Butylene glycol monomethacrylate | BGMA |
| 1,3-Butylene glycol dimethacrylate | BGDMA |
| Tetrahydrofurfuryl alcohol | THFA |
| Tetrahydrofurfuryl alcohol methacrylate | THFMA |
| TMPTMA + 1 Mol of MMA adduct | ADDUCT |

EXAMPLE 1

Trimethylolpropane (320 g), methyl methacrylate (1100 g) and p-methoxy phenol (0.146 g) were charged to a 2-liter reaction flask fitted with an air sparge, anchor stirrer, thermocouple and a packed distillation column.

The raw materials were dried to below 0.1% w/w moisture content by initially heating to 95° C. and re-

EXAMPLE 2

Using the same equipment described in Example 1 trimethylol propane (250 g), methyl methacrylate (1330 g) and p-methoxy phenol (1.25 g) were reacted using a mixture of lithium octanoate (39% in hydrocarbon solvent) (9.46 g) and calcium oxide (5.62 ) as catalyst. The reagents were not pre-dried prior to catalyst addition which was made to the reagents at ambient temperature. The mixture was heated to reflux with an air sparge and the azeotropic mixture of methanol and methyl methacrylate was removed from the top of the distillation column.

Only the initial dose of catalysts was used. Once the rate of methanol generation decreased to a minimum, the crude product was filtered to remove catalyst residues and excess methyl methacrylate was removed by heating under vacuum. The final product analysis was as follows:

| Catalyst w/w | Catalyst % on TMP | $Li^+:Ca^{++}$ Molar+ Ratio | Reflux Time Min | GC Anal. (%) | | | |
|---|---|---|---|---|---|---|---|
| | | | | TMPMMA | TMPDMA | TMPTMA | Adduct |
| Li-octoate: CaO, 1:1.5 | 3.7 | 1:3.7 | 945 | 0.3 | 14.7 | 79.4 | 3.7 |

EXAMPLE 3

Using a similar procedure to that stated in Example 2:
Trimethylolpropane (268 g, 2.0 mol) was reacted with methyl methacrylate (1400 g, 14.0 mol) using p- methoxyphenol (1.34 g, 0.5% on TMP) as part of the inhibition package. The reagents were not pre-dried and a single initial catalyst dose of lithium stearate (10.9 g) and calcium oxide (32.7 g) was added prior to heating and reaction. The final product analysis was found to be:

| Catalyst w/w | Catalyst % on TMP | Li+:Ca++ Molar+ Ratio | Reflux Time Min | GC Anal. (%) | | | |
|---|---|---|---|---|---|---|---|
| | | | | TMPMMA | TMPDMA | TMPTMA | Adduct |
| Li-stearate: CaO, 1:3 | 16.3 | 1:15.2 | 870 | 0.08 | 4.7 | 86.9 | 6.8 |

EXAMPLE 4

Using a similar procedure to that state in Example 2: Trimethylolpropane (250 g), methylmethacrylate (1330 g) and p-methoxy phenol (1.25 g) were reacted using a mixture of lithium octanoate solution (9.46 g) and calcium oxide (5.62 g) as catalyst. The reactants were not pre-dried prior to the initial catalyst charge. A second dose of catalyst mixture equal in weight to the initial charge was charged after 320 minutes at reflux. After reaction and work-up stages the final product analyses was as follows:

| Catalyst w/w | Catalyst % on TMP | Li+:Ca++ Molar Ratio | Reflux Time Min | GC Anal. (%) | | | |
|---|---|---|---|---|---|---|---|
| | | | | TMPMMA | TMPDMA | TMPTMA | Adduct |
| Li-octoate CaO, 1:3 | 12 | 1:3.7 | 740 | 0 | 1.2 | 92.3 | 4.5 |

EXAMPLE 5

Using a similar procedure to that stated in Example 2. The exact conditions in Example 3 were repeated but the second dose of catalyst was added after 430 mins of reaction. After reaction and work-up stages the final product analysis was as follows:

| Catalyst w/w | Catalyst % on TMP | Li+:Ca++ Molar Ratio | Reflux Time Min | GC Anal. (%) | | | |
|---|---|---|---|---|---|---|---|
| | | | | TMPMMA | TMPDMA | TMPTMA | Adduct |
| Li stearate: CaO, 1:3 | 32.6 | 1:15.6 | 540 | 0.03 | 3.7 | 90.3 | 4.8 |

EXAMPLE 6

Using a similar procedure to that stated in Example 2:

Trimethylol propane (250 g), methyl methacrylate (1330 g) and p-methoxy phenol (1.25 g) were reacted using a mixture of lithium nitrate (0.31 g) and calcium hydroxide (1.24 g) as catalyst. The reactants were not pre-dried prior to the catalyst charge.

Four extra doses of the catalyst mixture equal in weight to the initial charge were charged sequentially after 210, 275, 445 and 590 minutes respectively at reflux. After reaction and work-up stages the final product analysis was as follows:

| Catalyst w/w | Catalyst % on TMP | Li+:Ca++ Molar Ratio | Reflux Time Min | GC Anal. (%) | | | |
|---|---|---|---|---|---|---|---|
| | | | | TMPMMA | TMPDMA | TMPTMA | Adduct |
| LiNO3: Ca(OH)2, 1:4 | 3.1 | 1:3.76 | 770 | 0 | 1.7 | 96.3 | 1.5 |

EXAMPLE 7

Using a similar procedure to that stated in Example 2: Trimethylol propane (250 g), methyl methacrylate (1330 g) and p-methoxyphenol (1.25 g) were reacted using a mixture of lithium nitrate (1.88 g) and barium oxide (5.62 g) as catalyst. The reactants were not pre-dried prior to the catalyst addition.

One extra dose of the catalyst mixture was charged after 250 minutes and a half-dose each after 760 and 865 minutes at reflux. After reaction and work-up stages the final product analysis was as follows:

| Catalyst w/w | Catalyst % on TMP | Li+:Ba++ Molar Ratio | Reflux Time Min | GC Anal. (%) | | | |
|---|---|---|---|---|---|---|---|
| | | | | TMPMMA | TMPDMA | TMPTMA | Adduct |
| LiNO3: BaO, 1:3 | 9 | 1:1.34 | 990 | 0.1 | 5.67 | 89.2 | 3.5 |

EXAMPLE 8

Using a similar procedure to that stated in Example 2:

Trimethylolpropane (250 g), methyl methacrylate (1330 g) and p-methyxyphenol were reacted using a mixture of lithium nitrate (1.88 g) and calcium oxide (1.88 g) as catalyst. The reactants were not dried prior to catalyst addition.

| Catalyst w/w | Catalyst % on EG | Li$^+$:Ca$^{++}$ Molar Ratio | Reflux Time Min | GC Anal. (%) | | |
|---|---|---|---|---|---|---|
| | | | | EGMMA | EDGMA | Adduct |
| Li-benzoate: CaO, 1:3 | 6 | 1:6.86 | 620 | 3.3 | 87.7 | 2.2 |

An extra dose of catalyst equal in weight to the initial charge was charged after 300 minutes at reflux. After reaction and work-up stages the final product analysis was as follows:

| Catalyst w/w | Catalyst % on TMP | Li$^+$:Ca$^{++}$ Molar Ratio | Reflux Time Min | GC Anal. (%) | | | |
|---|---|---|---|---|---|---|---|
| | | | | TMPMMA | TMPDMA | TMPTMA | Adduct |
| LiNO$_3$: CaO$_2$ 1:1 | 3 | 1:1.24 | 465 | 0.2 | 6.1 | 91 | 2.2 |

EXAMPLE 9

Using a similar procedure to that stated in Example 2: Trimethylolpropane (250 g), methylmethacrylate (1330 g) and p-methoxy phenol (1.25 g) were reacted with a mixture of lithium oxide (1.88 g) and calcium nitrate (7.52 g) as catalyst. The reactants were not pre-dried prior to catalyst addition.

Three extra doses of catalyst equal in weight to the initial charge were added sequentially after 90, 520 and 860 minutes. After reaction and work-up stages the final product analysis was as follows:

| Catalyst w/w | Catalyst % on EG | Li$^+$:Ca$^{++}$ Molar Ratio | Reflux Time Min | GC Anal. (%) | | | |
|---|---|---|---|---|---|---|---|
| | | | | TMPMMA | TMPDMA | TMPTMA | Adduct |
| LiNO$_3$: Ca(NO$_3$)$_2$ 1:4 | 12 | 1:1.68 | 1010 | 0 | 5.4 | 92.3 | 1.7 |

EXAMPLE 10

Using a similar procedure to that stated in Example 2: Ethylene glycol (186 g), methyl methacrylate (1350 g) and p-methoxyphenol (1.54 g) were reacted with a mixture of lithium benzoate (1.4 g) and calcium oxide (4.19 g) as catalyst. The reactants were not dried prior to catalyst addition.

An extra dose of catalyst equal in weight to the initial charge was added after 620 minutes. After reaction and work-up stages the final product analysis was as follows:

EXAMPLE 11

Using a similar procedure to that stated in Example 2: 1,3-butyleneglycol (270 g), methyl methacrylate (1350 g) and p-methoxy phenol (1.35 g) were reacted using a mixture of lithium nitrate (2.03 g) and calcium oxide (6.09 g) as catalyst. The reactants were not pre-dried prior to catalyst addition.

An extra dose of catalyst equal in weight to the initial charge was added after 575 minutes at reflux. After reaction and work-up stages the final product analysis was as follows:

| Catalyst w/w | Catalyst % on BG | Li$^+$:Ca$^{++}$ Molar Ratio | Reflux Time Min | GC Anal. (%) | |
|---|---|---|---|---|---|
| | | | | BGMA | BGDMA |
| LiNO$_3$:CaO 1:3 | 6 | 1:3.7 | 575 | 0.7 | 91.1 |

EXAMPLE 12

Using a similar procedure to that stated in Example 2: Tetrahydrofurfuryl alcohol (275.4 g), methyl methacrylate (1350 g) and p-methoxy phenol (1.38 g) were reacted with a mixture of lithium nitrate (2.07 g) and calcium hydroxide (6.20 g) as catalyst. The reactants were not pre-dried prior to catalyst addition. An extra dose of catalyst equal in weight to the initial charge was added after 185 minutes at reflux. After reaction and work-up stages the final product analysis was as follows:

| Catalyst w/w | Catalyst % on THFA | Li$^+$:Ca$^{++}$ Molar Ratio | Reflux Time Min | GC Anal. (%) | | |
|---|---|---|---|---|---|---|
| | | | | THFA | THFMA | Adduct |
| LiNO$_3$: Ca(OH)$_2$, 1:3 | 6 | 1:2.8 | 435 | 0.67 | 96.9 | 1.0 |

EXAMPLE 13

Using a similar procedure to that stated in Example 2:

Trimethylolpropane (320 g) and methyl methacrylate (1100 g) were reacted using a mixture of lithium nitrate (1.2 g) and calcium oxide (3.6 g) as catalyst. The reactants were not pre-dried prior to the catalyst charge. The methyl methacrylate charge and that added during the reaction were distilled to remove any p-methoxyphenol. Thus no p-methoxyphenol was present during the reaction.

Further doses of lithium nitrate (0.6 g) and calcium oxide (1.8 g) were added after 2.5 hours, and a dose of lithium nitrate (1.2 g) and calcium oxide (3.6 g) after 4 hours and, another dose of the catalyst components in the respective proportion (0.8 g/2.4 g) was added after 10 hours.

After 12 hours the reaction product work-up stage was carried out.

An air sparge was used throughout the reaction and work-up stages.

The final product had an assay of 93.2% of TMPTMA, colour of 15 Hazen and peroxide content of 2 ppm.

I claim:

1. A process for the preparation of acrylic acid or methacrylic acid esters in an alcohol which has at least 2 carbon atoms and at least two oxygen functions which process comprises reacting under transesterification conditions a first reactant which is a preformed ester of (meth)acrylic acid and a $C_1$ to $C_4$ monohydric alcohol having only one oxygen function with a second reactant which is an alcohol having at least 2 carbon atoms and at least two oxygen functions in the presence of a catalyst composition comprising:
   a. an oxide, hydroxide or nitrate of calcium or barium and
   b. a lithium compound LiX, wherein X in LiX is selected from the anions nitrate and sulphite, such that both (a) and (b) are not nitrates in the same catalyst.

2. A process for the preparation of acrylic acid or methacrylic acid esters in an alcohol which has at least 2 carbon atoms and at least two oxygen functions which process comprises reacting under transesterification conditions a first reactant which is a preformed ester of (meth)acrylic acid and a $C_1$ to $C_4$ monohydric alcohol having only one oxygen function with a second reactant which is an alcohol having at least 2 carbon atoms and at least two oxygen functions in the presence of a catalyst composition comprising a mixture of lithium nitrate and calcium oxide.

* * * * *